US006961124B2

(12) United States Patent
Engelhardt et al.

(10) Patent No.: US 6,961,124 B2
(45) Date of Patent: Nov. 1, 2005

(54) METHOD FOR EXAMINING A SPECIMEN, AND SCANNING MICROSCOPE SYSTEM

(75) Inventors: Johann Engelhardt, Schoenborn (DE); Juergen Hoffmann, Wiesbaden (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 195 days.

(21) Appl. No.: 10/133,654

(22) Filed: Apr. 26, 2002

(65) Prior Publication Data
US 2002/0180965 A1 Dec. 5, 2002

(30) Foreign Application Priority Data
Apr. 26, 2001 (DE) .................. 101 20 425

(51) Int. Cl.$^7$ ............................ G01J 3/30; G01N 21/64
(52) U.S. Cl. .................... 356/417; 250/459.1; 359/326
(58) Field of Search ............... 356/417, 317–318; 250/458.1–461.2; 422/82.07–82.08; 359/326–332, 359/368

(56) References Cited

U.S. PATENT DOCUMENTS

| | | | |
|---|---|---|---|
| 5,034,613 A | 7/1991 | Denk et al. | |
| 5,304,810 A | 4/1994 | Amos | |
| 5,796,477 A | 8/1998 | Teich et al. | |
| 5,886,784 A | 3/1999 | Engelhardt | |
| 5,891,738 A | 4/1999 | Soini et al. | |
| 6,020,591 A * | 2/2000 | Harter et al. | 250/458.1 |
| 6,154,310 A | 11/2000 | Galvanauskas et al. | |
| 6,159,686 A * | 12/2000 | Kardos et al. | 250/484.2 |
| 6,166,385 A | 12/2000 | Webb et al. | |
| 6,169,289 B1 | 1/2001 | White et al. | |
| 6,344,653 B1 * | 2/2002 | Webb et al. | 250/458.1 |
| 6,405,070 B1 * | 6/2002 | Banerjee | 600/407 |

(Continued)

FOREIGN PATENT DOCUMENTS

DE  195 20 563  12/1996

(Continued)

OTHER PUBLICATIONS

Centonze, Victoria E. et al. , "Multiphoton Excitation provides optical sections from deeper within scattering specimens than confocal imaging" Biophys J. Oct. 1998., p. 2015-2024, vol. 75, No. 4, http://www.biophysj.org/cgi/content/full/75/4/2015, Nov. 24, 2003.

(Continued)

*Primary Examiner*—Gregory J. Toatley, Jr.
*Assistant Examiner*—Kara E. Geisel
(74) *Attorney, Agent, or Firm*—Simpson & Simpson, PLLC (57) ABSTRACT

A method for examining a specimen (27) that exhibits at least two optical transition lines and is optically excitable at least with light of a first and light of a second wavelength is characterized by the step of illuminating the specimen (27) with illuminating light (15) that generates at least a multiple of the first wavelength and a multiple of the second wavelength; and by the step of detecting the detected light (29) proceeding from the specimen (27).

Also disclosed is a scanning microscope system (1) having at least one light source (3) that emits illuminating light (15) for illumination of a specimen (27), the specimen (27) exhibiting at least two optical transition lines and being optically excitable at least with light of a first and light of a second wavelength, having at least one detector (41, 43, 65, 77, 79) for detection of the detected light (29) proceeding from the specimen (27) and an objective (25) for focusing the illuminating light (15) onto a subregion of the specimen (27). The scanning microscope system is characterized in that the illuminating light (15) generates at least a multiple of the first wavelength and a multiple of the second wavelength.

24 Claims, 5 Drawing Sheets

U.S. PATENT DOCUMENTS 6,528,802 B1 * 3/2003 Koenig et al. ........... 250/459.1
6,667,830 B1 * 12/2003 Iketaki et al. ............ 250/458.1

FOREIGN PATENT DOCUMENTS

| DE | 196 21 512 | 12/1997 |
|---|---|---|
| DE | 4414940 | 7/1998 |
| DE | 19902625 | 9/1999 |
| EP | 0495930 | 4/1999 |

OTHER PUBLICATIONS

Shear, Jason B., "Multiphoton Excited Fluorescence in Bioanylytical Chemistry" Analyical Chemistry News and Features, Sep. 1, 1999; pp598A-605A.

* cited by examiner

METHOD FOR EXAMINING A SPECIMEN, AND SCANNING MICROSCOPE SYSTEM

CROSS REFERENCE TO RELATED APPLICATIONS

This application claims priority of the German patent application 101 20 425.6 which is incorporated by reference herein.

FIELD OF THE INVENTION

The invention concerns a method for examining a specimen that exhibits at least two optical transition lines and is optically excitable at least with light of a first and light of a second wavelength.

The invention further concerns a scanning microscope system.

BACKGROUND OF THE INVENTION

For the examination of biological specimens, it has been usual for some time to prepare the specimen with optical markers, in particular with fluorescent dyes. Often, for example in the field of genetic investigations, several different fluorescent dyes which become attached to specific specimen constituents are introduced into the specimen. From the fluorescent properties of the prepared specimen it is possible, for example, to draw conclusions as to the nature and composition of the specimen, or as to concentrations of specific substances within the specimen.

In scanning microscopy, a specimen is illuminated with a light beam in order to observe the detected light (in the form of reflected or fluorescent light) emitted by the specimen. The focus of an illuminating light beam is moved in a specimen plane by means of a controllable beam deflection device, generally by tilting two mirrors; the deflection axes are usually perpendicular to one another, so that one mirror deflects in the X and the other in the Y direction. Tilting of the mirrors is brought about, for example, by means of galvanometer positioning elements. The power level of the detected light coming from the specimen is measured as a function of the position of the scanning beam. The positioning elements are usually equipped with sensors to ascertain the present mirror position.

In confocal scanning microscopy specifically, a specimen is scanned in three dimensions with the focus of a light beam.

A confocal scanning microscope generally comprises a light source, a focusing optical system with which the light of the source is focused onto a pinhole (called the "excitation pinhole"), a beam splitter, a beam deflection device for beam control, a microscope optical system, a detection pinhole, and the detectors for detection of the reflected or fluorescent light. The illuminating light is coupled in via a beam splitter. The fluorescent or reflected light coming from the specimen travels via the beam deflection device back to the beam splitter, passes through the latter and is focused onto the detection pinhole, behind which the detectors are located. This detection arrangement is called a "descan" arrangement. Detected light that does not originate directly from the focus region takes a different light path and does not pass through the detection pinhole, so that point like information is obtained which, by sequential scanning of the specimen with the focus of the illuminating light beam, results in a three-dimensional image. A three-dimensional image is usually achieved by acquiring image data in layers. Commercial scanning microscopes usually comprise a scan module that is flange-mounted onto the stand of a conventional light microscope and contains all the aforesaid elements additionally necessary for scanning a specimen.

In confocal scanning microscopy, a detection pinhole can be dispensed with in the case of two-photon (or multi-photon) excitation, since the excitation probability depends on the square of the photon density and thus on the square of the illuminating light intensity, which of course is much greater at the focus than in the adjacent regions. The fluorescent light being detected therefore very probably originates almost exclusively from the focus region, which renders superfluous any further differentiation, using a pinhole arrangement, between fluorescent photons from the focus region and fluorescent photons from the adjacent regions.

For simultaneous illumination with light of several wavelengths, several lasers are usually used. EP 0 495 930 "Confocal microscope system for polychromatic fluorescence" discloses an arrangement having a single laser that emits several laser lines. In practice, mixed-gas lasers, in particular ArKr lasers, are used for this purpose. For detection, several detectors are usually provided for detected light of different wavelengths. One particularly flexible arrangement for simultaneous polychromatic detection of detected light of several wavelengths is disclosed in German Patent DE 199 02 625 "Apparatus for simultaneous detection of several spectral regions of a laser beam."

Many fluorescent dyes can be excited only with ultraviolet illuminating light. The use of ultraviolet illuminating light has the disadvantage, especially for living specimens, of much more severe specimen damage. In addition, all optical components must be transparent to ultraviolet light and to the fluorescent light, which because of Stokes shifting has a longer wavelength, and must not be damaged by illumination with ultraviolet light. With cemented optical components in particular, such as lens element groups in a microscope objective, illumination with ultraviolet light results in irreversible damage to the cement and the lens elements. A further disadvantage of illumination with ultraviolet light arises from its shallower penetration depth into biological specimens. The disadvantages can be eliminated using two-photon or multi-photon excitation. In multi-photon scanning microscopy, the fluorescent photons attributable to a two-photon or multi-photon excitation process are detected. The probability of a two-photon transition depends on the square of the excitation light power level. In order to achieve high light power levels, it is therefore advantageous to pulse the illuminating light in order to achieve high peak pulse power levels. This technique is known, and is disclosed e.g. in U.S. Pat. No. 5,034,613 "Two-photon laser microscopy" and in the German Patent Application DE 44 14 940. A further advantage of multi-photon excitation, in confocal scanning microscopy in particular, is improved bleaching characteristics, since the specimen bleaches out only in the region of sufficient power density, i.e. at the focus of an illuminating light beam. In contrast to single-photon excitation, almost no bleaching takes place outside this region.

All known methods and arrangements for examination of a specimen based on multi-photon excitation are limited to excitation of a single laser line. For many applications, it is essential to mark the specimen specifically with different fluorescent dyes or other markers, in order to obtain information concerning the three-dimensional structure or composition of the specimen by simultaneous excitation of all the fluorescent dyes and polychromatic detection. Simultaneous excitation of several UV fluorescent dyes is at present possible only with single-photon excitation, so that the negative effects of irradiation with ultraviolet light are fully evident.

SUMMARY OF THE INVENTION

It is therefore the object of the invention to propose a method that makes possible simultaneous polychromatic detection with improved bleaching characteristics, in particular in the context of specimens excitable in the ultraviolet spectral region.

The aforesaid object is achieved by means of a method which comprises the steps of:
   illuminating the specimen with an illuminating light that generates at least a multiple of the first wavelength and a multiple of the second wavelength; and
   detecting a detection light proceeding from the specimen.

It is moreover an object of the invention to describe a scanning microscope system that makes possible simultaneous polychromatic detection with improved bleaching characteristics, in particular in the context of specimens excitable in the ultraviolet spectral region.

This object is achieved by means of a scanning microscope system comprising.
   a specimen exhibiting at least two optical transition lines and optically excitable with light of at least a first wavelength and light of at least a second wavelength;
   at least one light source that emits an illuminating light for illumination of the specimen;
   at least one detector for detection of the detected light proceeding from the specimen and;
   an objective for focusing the illuminating light onto a subregion of the specimen, wherein the illuminating light generates at least a multiple of the first wavelength and a multiple of the second wavelength.

The invention has the advantage that specimens marked with different fluorescent dyes can be examined in the context of simultaneous excitation and substantially improved bleaching characteristics.

In a further method step, the illuminating light is focused onto a subregion of the specimen, thereby resulting in a higher power density and thus a higher probability of multi-photon excitation. In a further step, the specimen is scanned by successively guiding the illuminating light over several subregions. A beam deflection device having rotatably mounted mirrors that are driven by galvanometers preferably serves to guide the illuminating light.

A variant embodiment in which detection of the light proceeding from the specimen is accomplished confocally is very particularly advantageous. For this purpose, a detection pinhole which allows the passage only of light that derives from the illuminated subregion is arranged in front of the detectors. Another embodiment operates in the so-called "non-descan" detection mode without a detection pinhole. Since the excitation probability of, for example, a two-photon excitation depends on the square of the photon density and thus on the square of the illuminating light intensity, which of course is much greater at the focus than in the adjacent regions, the light striking the detector very probably derives almost exclusively from the focus region, which renders superfluous any further differentiation, by means of a pinhole arrangement, between fluorescent photons from the focus region and fluorescent photons from the adjacent regions.

In an embodiment, dichroic filters which allocate the detected light proceeding from the specimen, which contains several wavelengths, to several detectors according to wavelength or according to individual wavelength regions, are provided for detection. The detectors can be, for example, photomultipliers or semiconductor detectors, such as photodiodes or avalanche photodiodes. They convert the detected light into a detected signal whose amplitude depends on—preferably is proportional to—the power level of the detected light. In a very particularly preferred embodiment, the detector is a multi-band detector.

As the specimen is scanned, the detected signals are associated with the position of the scanned subregions so that the detected signals can be displayed on a display arranged into a two- or three-dimensional image.

In a further preferred embodiment, the illuminating light is pulsed. For this purpose, the light source contains at least two pulsed lasers which emit light pulse trains that generate a multiple of the first and a multiple of the second wavelength, the light pulse trains being combined into an illuminating light beam using a dichroic beam splitter. The pulsed lasers are preferably embodied in such a way that the light pulses are shorter than 1 picosecond.

In another variant embodiment, the light source contains only one pulsed laser which simultaneously emits light of the required wavelengths.

In a very particularly preferred embodiment, the light source contains a pulsed laser and a beam splitter arranged thereafter, which splits the emitted light into a first and second beam segment. A wavelength-modifying means, for example an optically parametric oscillator or a crystal for frequency multiplication, is arranged in one of the beam paths of the beam segments.

Also particularly advantageous is a variant embodiment in which the light source encompasses a microstructured optical element onto which the light of a laser is focused, such that a conversion into light of other wavelengths, preferably into a broad wavelength spectrum, takes place in the microstructured optical element.

In a preferred embodiment of the scanning microscope system, the microstructured optical element is constructed from a plurality of microoptical structural elements which have at least two different optical densities. A very particularly preferred embodiment is one in which the optical element contains a first region and a second region, in which context the first region has a homogeneous structure, and a microscopic structure made up of microoptical structural elements is formed in the second region. It is also advantageous if the first region surrounds the second region. The microoptical structural elements are preferably cannulas, lands, honeycombs, tubes, or cavities.

In another embodiment, the microstructured optical element comprises glass or plastic material and cavities arranged next to one another. Particularly preferable is the variant embodiment in which the microstructured optical element is made of photonic band gap material and is configured as a light-guiding fiber. An optical diode which suppresses return reflections of the light beam deriving from the ends of the light-guiding fiber is preferably provided between the laser and the light-guiding fiber.

A very particularly preferred and easily implemented variant embodiment contains as the microstructured optical element a conventional light-guiding fiber having a fiber core diameter of approx. 9 $\mu$m, which has a taper along at least a portion. Light-guiding fibers of this kind are known as "tapered fibers." The light-guiding fiber is preferably 1 m long in total, and has a taper over a length of 30 to 90 mm. In a preferred embodiment, the diameter of the entire fiber in the region of the taper is approx. 2 $\mu$m.

In a further embodiment, at least some of the photons of the illuminating light are entangled. U.S. Pat. No. 5,796,477 discloses an entangled-photon microscope that possesses the advantages of multi-photon excitation but avoids extremely high excitation light power levels and the disadvantages associated therewith. Instead of photons created independently of one another, entangled photons are used to excite the specimen. The photons are in a so-called "quantum mechanically entangled" state. When illumination with entangled photons is used, the probability of excitation of a fluorophore in the specimen depends linearly on the excitation light power level and not, as in the case of known two-photon excitation, on the square of the excitation light power level, since in principle, when the boundary conditions are suitable, entangled photons at the focus are always coordinated with one another in terms of time and place.

BRIEF DESCRIPTION OF THE DRAWINGS

The subject matter of the invention is depicted schematically in the drawings and will be described below with reference to the Figures, identically functioning elements being labeled with the same reference characters. In the drawings.

DETAILED DESCRIPTION OF THE INVENTION

Figure 1:
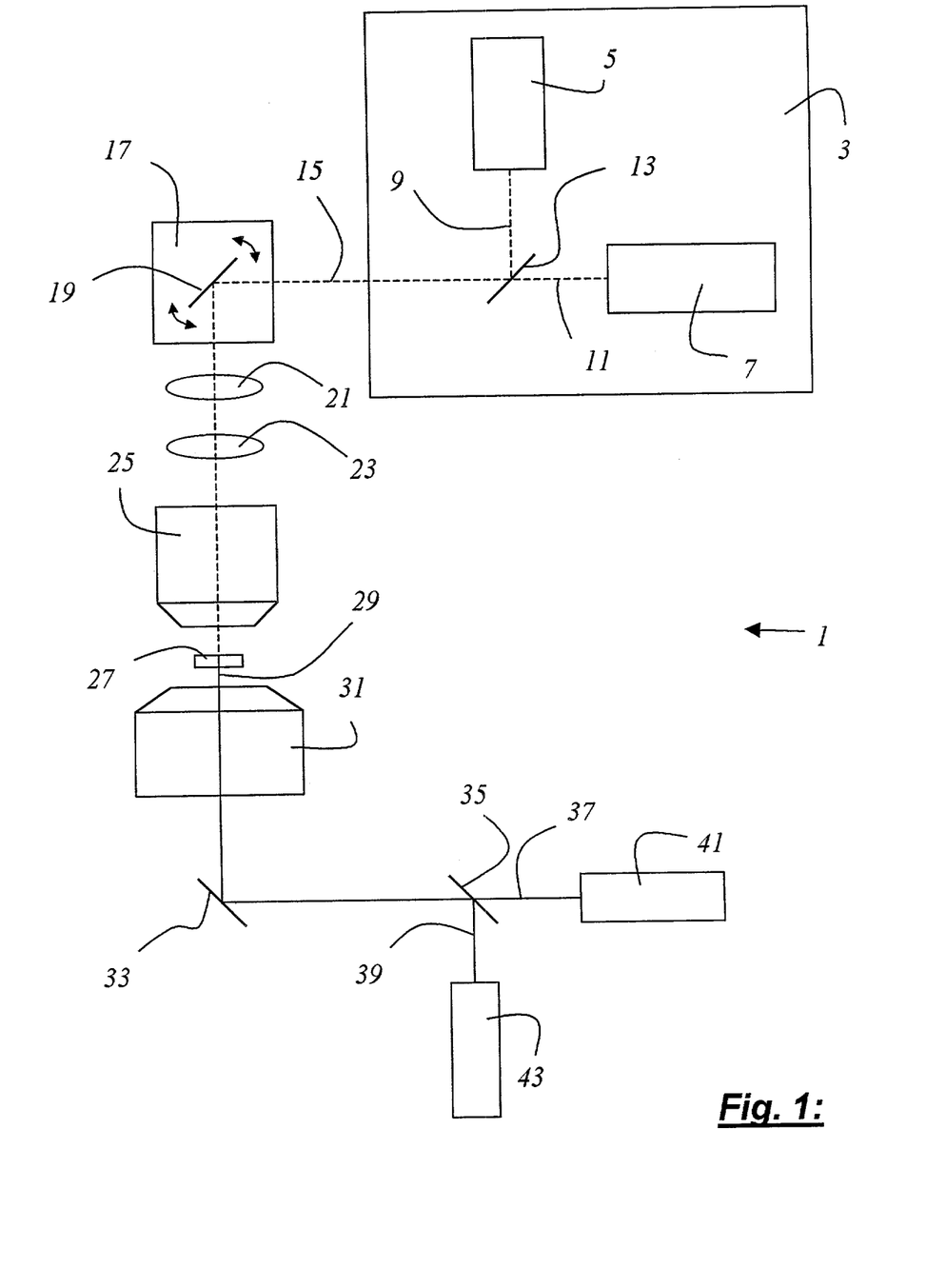
FIG. 1 shows a scanning microscope system according to the present invention.

FIG. 1 schematically shows a scanning microscope system 1 according to the present invention having a light source 3 that contains a first and second laser 5, 7 embodied as mode-locked titanium/sapphire lasers. Light 9 emitted by first laser 5, which has a wavelength of 780 nm, and light 11 emitted by second laser 7, which has a wavelength of 960 nm, are combined with a dichroic beam splitter 13 into illuminating light 15. Illuminating light 15, shaped into a beam, arrives at a beam deflection device 17 that contains a gimbal-mounted mirror 19. By means of scanning optical system 21, tube optical system 23, and objective 25, illuminating light 15 that has been shaped into a beam is guided over or through specimen 27, which contains two fluorescent dyes that are optically excitable at 390 nm and 480 nm respectively. Detected light 29 proceeding from specimen 27 is collimated by a condenser 31 and reflected by a mirror 33 to a dichroic beam splitter 35 that divides the detected light spatially and spectrally into two detected light beam segments 37, 39, which are detected by two detectors 41, 43 (both embodied as photomultipliers) and converted into electrical signals proportional in amplitude to the power level of detected light beam segments 37, 39 respectively.

Figure 2:
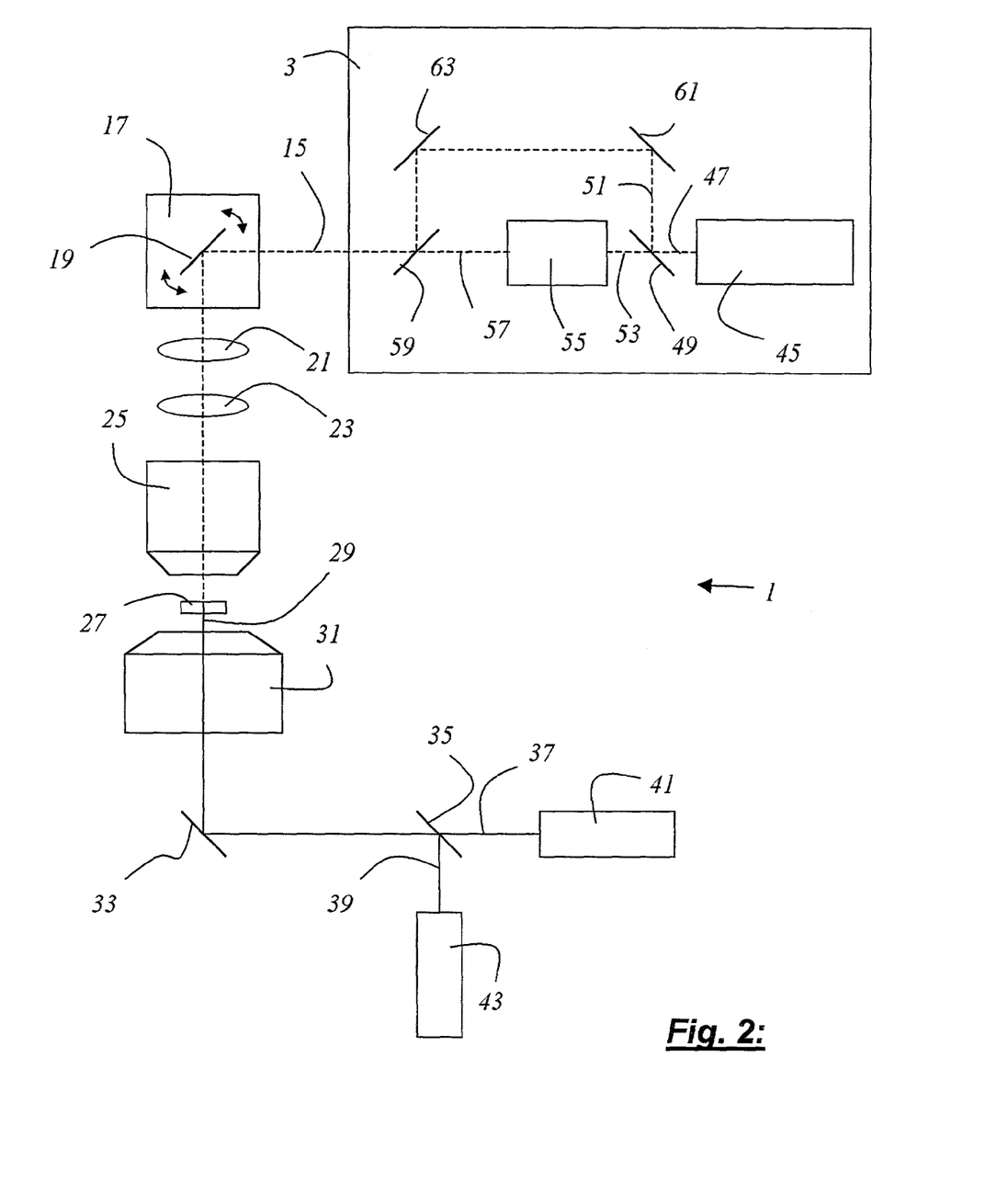
FIG. 2 shows a further scanning microscope system according to the present invention.

FIG. 2 shows a scanning microscope system 1 according to the present invention that also, like the scanning microscope shown in FIG. 1, operates in non-descan detection mode. Light source 3 of this embodiment contains a laser 45 that is embodied as a mode-locked titanium-sapphire laser. Light 47 of laser 45 is divided with a beam splitter 49 into a first and second light beam segment 51 and 53. Light beam segment 53 arrives at an optically parametric oscillator 55. Light beam segment 57 emerging from optically parametric oscillator 55 is directed to a dichroic beam combiner 59 where it is combined with first light beam segment 51, which is directed via mirrors 61 and 63, to form illuminating light 15.

Figure 3:
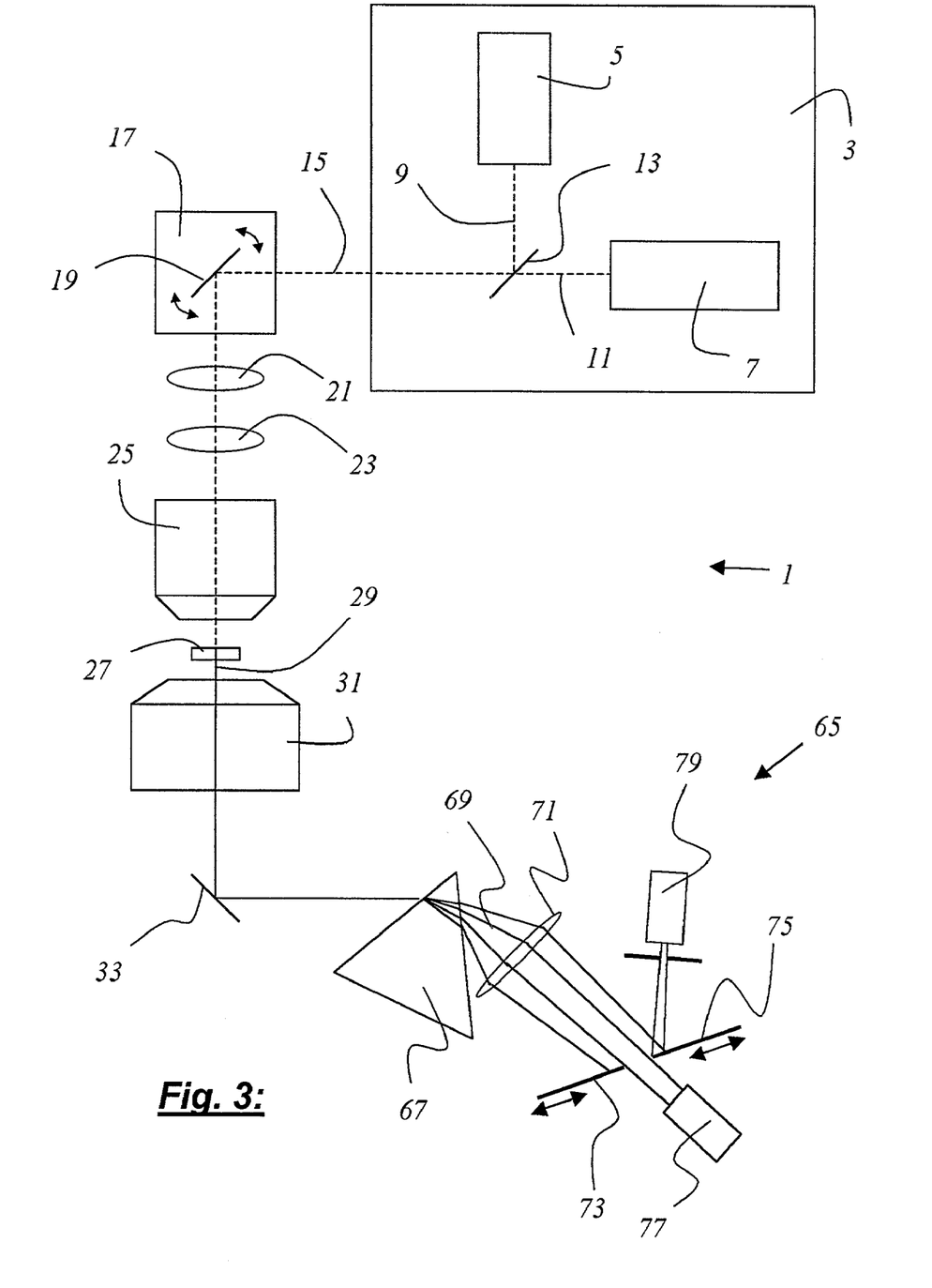
FIG. 3 shows a further scanning microscope system according to the present invention having a multi-band detector.

FIG. 3 shows a scanning microscope system 1 according to the present invention that also, like the scanning microscope shown in FIG. 1, operates in non-descan detection mode. A multi-band detector 65 is provided for detection. Detected light 29 is divided spatially and spectrally with a prism 67. A further possibility for spectral division is the use of a reflection grating or transmission grating. The spectrally divided light fan 69 is focused with focusing optical system 71, and then strikes a mirror stop arrangement 73, 75. Mirror stop arrangement 73, 75, the means for spectral spatial division (prism 67), focusing optical system 71, and detectors 77 and 79 are together designated as multi-band detector 65. A portion of the divided light fan 69 of detected light 29, which comprises only light of a preselected spectral region, passes through the mirror stop arrangement and is detected by detector 77, which is embodied as a photomultiplier. Another portion of the divided light fan 69 is reflected at mirror stop arrangement 75 and arrives at detector 79, which is also embodied as a photomultiplier. The mirror stop arrangements are displaceable in the directions illustrated by the double arrows, so that the spectral detection regions of the light delivered to detectors 77, 79 are continuously adjustable. It is possible (although not depicted for reasons of clarity) also to install further detectors and to provide further mirror stops. Electrical detected signals proportional to the power level of detected light 29 of the respective spectral region proceeding from specimen 27 are generated in detectors 77, 79 and are associated, in a control and processing unit (not shown), with the position signals sensed in the beam deflection device by means of a position sensor. They are then assembled into an image using a PC. This operation is familiar to those skilled in the art, and for the sake of clarity is not depicted. Also omitted in the interest of better presentation are certain optical elements for guiding and shaping the light beams, which are sufficiently familiar to those skilled in this art.

Figure 4:
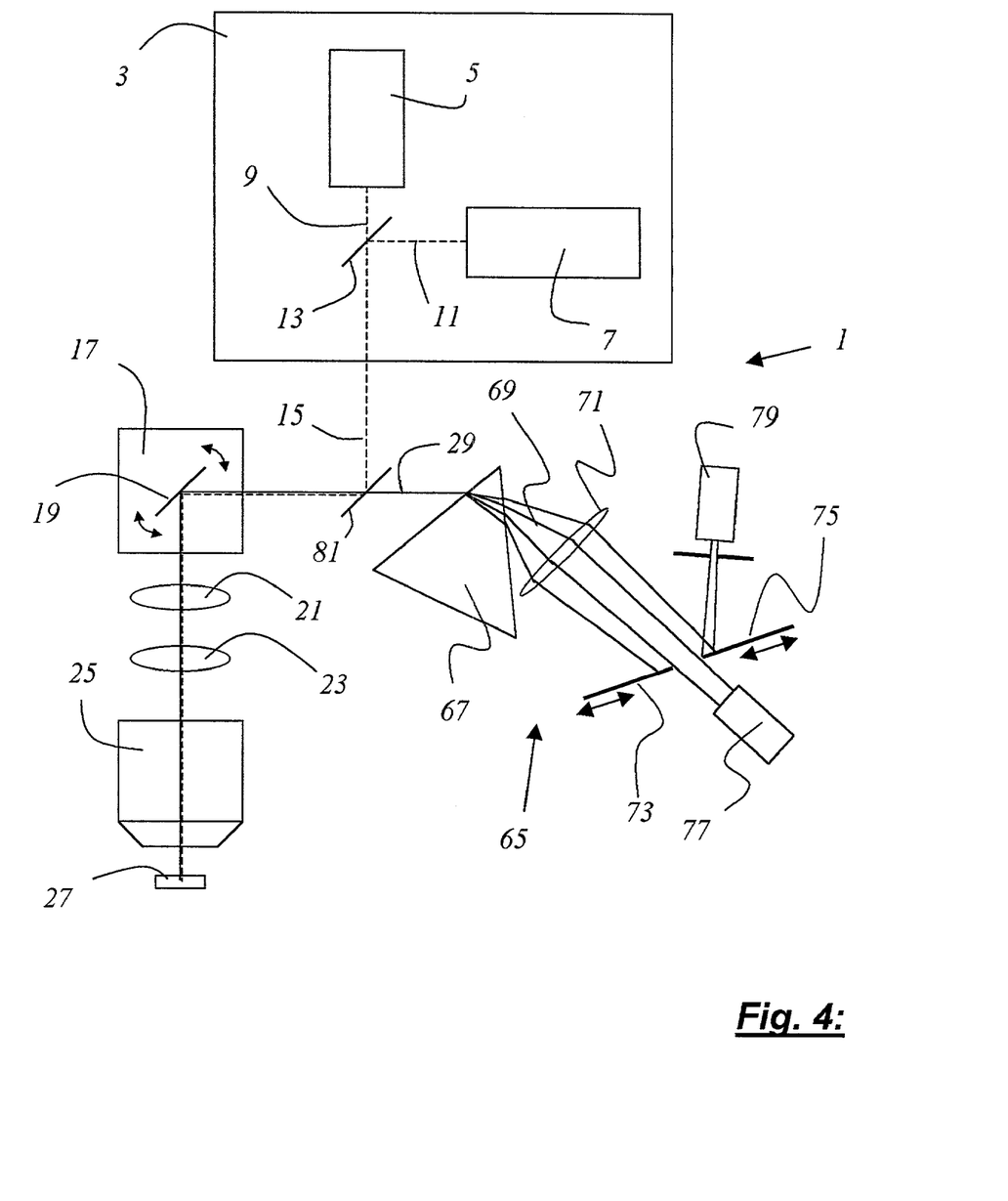
FIG. 4 shows a further scanning microscope system according to the present invention having a multi-band detector.

FIG. 4 shows a scanning microscope system according to the present invention with descan detection. Illuminating light 15 of light source 3 is reflected by a dichroic beam splitter 81 to beam deflection device 17 and directed by the latter, through scanning optical system 21, tube optical system 23, and objective 25, over or through specimen 27. Detected light 29 proceeding from specimen 27 travels along the same light path via beam deflection device 17 back to dichroic beam splitter 81, passes through the latter and the detection pinhole (not shown in the interest of clarity), and then strikes multi-band detector 65.

Figure 5:
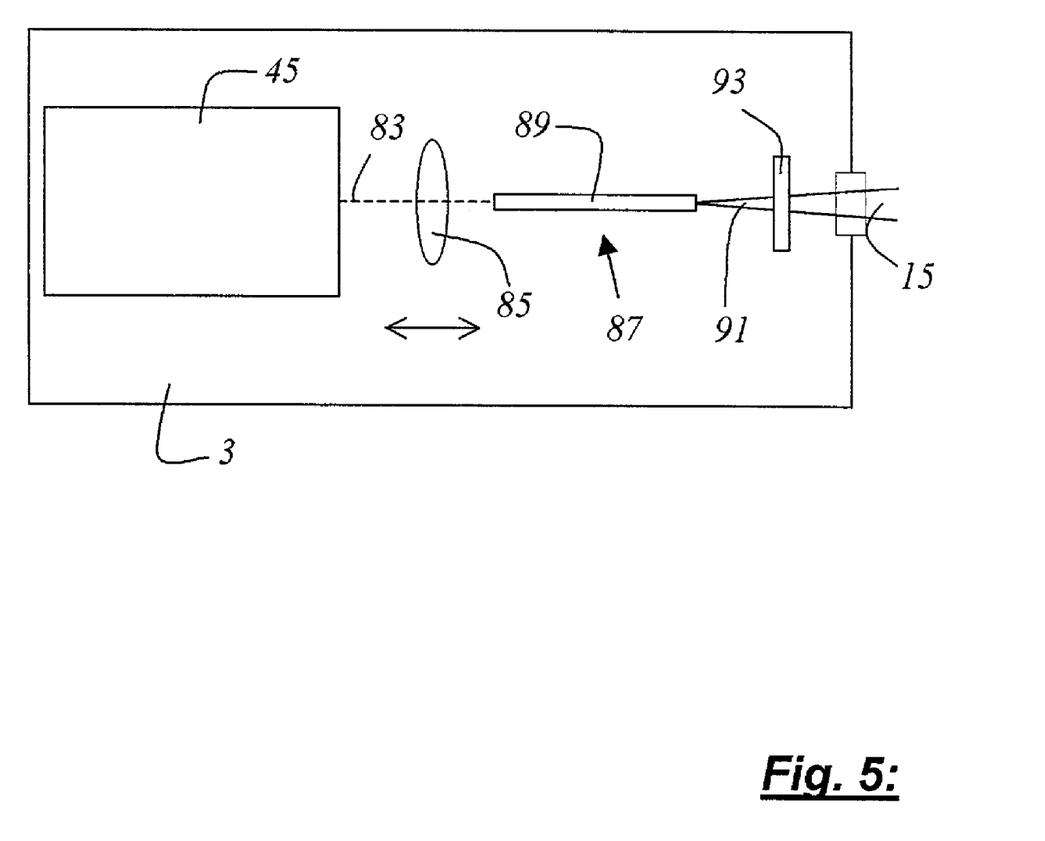
FIG. 5 shows a light source for a scanning microscope system according to the present invention.

FIG. 5 shows a light source 3 for a scanning microscope system 1 according to the present invention, which contains a laser 45 that is embodied as a diode-laser-pumped, mode-locked titanium:sapphire laser and emits a pulsed light beam 83 that is shown as a dashed line. The duration of the light pulses is approximately 100 femtoseconds at a repetition rate of approx. 80 MHz. Light beam 83 is focused with focusing optical system 85, which is configured as a zoom optical system and is arranged displaceably along the propagation direction of the light beam, onto a microstructured optical element 87 that comprises a light-guiding fiber 89 made of photonic band gap material. In microstructured optical element 87, the light of the laser is spectrally spread. From the spectrum of spectrally spread light 91, which comprises wavelengths from approx. 300 nm to 1600 nm, a bandpass filter 93 is used to filter out light of two wavelengths suitable for illumination according to the present invention, which constitutes illuminating light 15.

The invention has been described with reference to a particular embodiment. It is self-evident, however, that changes and modifications can be made without thereby leaving the range of protection of the following claims.

What is claimed is:

1. A method for examining a specimen that exhibits at least two optical transition lines and is optically excitable with light of at least a first and light of a second wavelength, the method comprises the steps of:

illuminating the specimen with an illuminating light composed of at least a multiple of the first wavelength and a multiple of the second wavelength, wherein a portion of said illuminating light is produced by a microstructured optical element, said microstructured optical element constructed from a plurality of microoptical structural elements having at least two different optical densities that converts light impinging thereon into light of at least one other wavelength; and, detecting a detection light proceeding from the specimen.

2. The method as defined in claim 1, wherein a further step comprises focusing the illuminating light onto a subregion of the specimen.

3. The method as defined in claim 1, wherein a step further comprises:

scanning the specimen by successively guiding the illuminating light over several subregions.

4. The method as defined in claim 1, wherein the detecting is accomplished confocally.

5. The method as defined in claim 1, wherein further steps comprise:

converting the detection light into detected signals having an amplitude which depends on a power level of the detection light; and associating the detected signals with a scanned subregion.

6. The method as defined in claim 1, wherein at least two detection channels are provided and the detecting is accomplished in as a function of the wavelength of the detected light.

7. The method as defined in claim 1, wherein the illuminating light is pulsed.

8. The method as defined in claim 1, wherein the specimen contains an optically excitable marker or a fluorescent dye.

9. The method as defined in claim 1, wherein the illuminating light is double the first wavelength and double the second wavelength.

10. The method as defined in claim 1, wherein the illuminating light is triple the first wavelength and triple the second wavelength.

11. The method as defined in claim 1, wherein the illuminating light contains entangled photons.

12. A scanning microscope system comprising:

a specimen exhibiting at least two optical transition lines and being optically excitable with light of at least a first and light of at least a second wavelength;

at least one light source that emits a light for illumination of the specimen; at least one microstructured optical element that converts a portion of said light to light of at least one other wavelength, said microstructured optical element constructed from a plurality of microoptical structural elements having at least two different optical densities;

at least one detector for detection of the detected light proceeding from the specimen and;

an objective for focusing said light and said light of at least one other wavelength onto a subregion of the specimen, wherein said light and said light of at least one other wavelength comprise at least a multiple of the first wavelength and a multiple of the second wavelength.

13. The scanning microscope system as defined in claim 12, wherein the light source contains at least one laser that repetitively emits light pulses.

14. The scanning microscope system as defined in claim 13, wherein the light pulses are shorter in time than 1 picosecond.

15. The scanning microscope system as defined in claim 12, wherein the microstructured optical element has a first region and a second region, in which context the first region has a homogeneous structure, and a microscopic structure made up of microoptical structural elements is formed in the second region.

16. The scanning microscope system as defined in claim 15, wherein the first region surrounds the second region.

17. The scanning microscope system as defined in claim 12, wherein the microstructured optical element is made from glass or plastic material and cavities arranged next to one another.

18. The scanning microscope system as defined in claim 12, wherein the microoptical structural elements are cannulas, lands, honeycombs, tubes, or cavities.

19. The scanning microscope system as defined in claim 12, wherein the microstructured optical element is made of photonic band gap material.

20. The scanning microscope system as defined in claim 12, wherein the microstructured optical element is configured as a light-guiding fiber.

21. The scanning microscope system as defined in claim 20, wherein the light-guiding fiber has a taper.

22. The scanning microscope system as defined in claim 12, wherein the illuminating light comprises at least double the first wavelength and at least double the second wavelength.

23. The scanning microscope system as defined in claim 12, wherein the illuminating light comprises at least triple the first wavelength tripled and at least triple the second wavelength.

24. The scanning microscope system as defined in claim 12, wherein the detector is a multi-band detector.

* * * * *